United States Patent
Petrus

(10) Patent No.: US 6,346,519 B1
(45) Date of Patent: Feb. 12, 2002

(54) METHOD AND COMPOSITION FOR TREATING ARTHRITIS

(75) Inventor: Edward J. Petrus, Austin, TX (US)

(73) Assignee: Advanced Medical Instruments, Austin, TX (US)

( * ) Notice: Subject to any disclaimer, the term of this patent is extended or adjusted under 35 U.S.C. 154(b) by 0 days.

(21) Appl. No.: 09/350,380

(22) Filed: Jul. 8, 1999

Related U.S. Application Data

(63) Continuation-in-part of application No. 09/149,241, filed on Sep. 9, 1998, now abandoned.

(51) Int. Cl.$^7$ ............................................. A61K 31/73
(52) U.S. Cl. ........................ 514/62; 514/61; 514/825; 514/885
(58) Field of Search ............................ 514/2, 62, 494, 514/885

(56) References Cited

U.S. PATENT DOCUMENTS

| | | | |
|---|---|---|---|
| 3,859,436 A | 1/1975 | Jacobi | 514/23 |
| 4,006,224 A | 2/1977 | Prudden | 514/62 |
| 4,079,125 A | 3/1978 | Sipos | 424/480 |
| 4,489,065 A | 12/1984 | Walton et al. | 514/34 |
| 4,590,067 A | 5/1986 | Meisner | 424/54 |
| 4,775,536 A | 10/1988 | Patell | 424/471 |
| 4,870,061 A | 9/1989 | Speck | 514/62 |
| 5,036,056 A | 7/1991 | Kludas | 514/54 |
| 5,225,202 A | 7/1993 | Hodges et al. | 424/480 |
| 5,266,594 A | 11/1993 | Dawson et al. | 514/560 |
| 5,356,634 A | 10/1994 | Wu et al. | 424/464 |
| 5,449,688 A | 9/1995 | Wahl et al. | 514/546 |
| 5,468,476 A | 11/1995 | Amluwalia et al. | 424/73 |
| 5,545,614 A | 8/1996 | Stawler et al. | 514/6 |
| 5,585,402 A | 12/1996 | Moncada et al. | 514/564 |
| 5,665,757 A | 9/1997 | Dunn et al. | 514/403 |
| 5,679,344 A | 10/1997 | Williams et al. | 424/94.63 |
| 5,723,151 A | 3/1998 | Cook et al. | 424/459 |
| 5,723,451 A | 3/1998 | Mjalli et al. | 514/255 |
| 5,795,576 A | 8/1998 | Diaz et al. | 424/195.1 |
| 5,804,594 A | 9/1998 | Murad | 514/474 |
| 5,840,715 A | 11/1998 | Florio | 514/62 |
| 5,888,514 A | 3/1999 | Weisman | 424/195.1 |
| 5,891,441 A | 4/1999 | Diaz et al. | 424/195.1 |
| 5,891,861 A | 4/1999 | Plats | 514/55 |

OTHER PUBLICATIONS

Chavez, M. "Glucosamine Sulfate and Chondroitin Sulfates", Hospital Pharmacy, vol. 32, No. 9, pp. 1275–1285, 1997.*

Cuanjungco et al., "Zinc metabolism in the brain: relevance to human neurodegenerative disorders", Neurobiol. Dis., vol. 4(3–4), pp. 137–169, 1997.*

Da Camara et al., "Glucosamine sulfate for osteoarthritis", Ann. Pharmacother., vol. 32(5), pp. 580–587, 1998.*

Sharif et al., "Terminal N–Acetylglucosamine in Chronic Synovitis", British Journal of Rheumatology, vol. 29(1): 25–31, 1990.*

Studer RK, Georgeson HI, Miller LA, Evans CH, Inhibitory Of Transforming Growth Factor B Production By Nitric Oxide Treated Chondrocytes. Arthritis & Rheumatism; 42(2):248–257, 1999.

St. Clair EW, Nitric Oxide—Friend Or Foe In Arthritis? J. Of Rheumatology 1998; 25(8):1451–1453.

Henrotin Ye, et al, Nitak Oxide Downregulatus Cytokings. J of Rheumatology 1998; 25(8):1595–1601.

Yamaguchi M, Role Of Zinc In Bone Formation and Bone Resorption, J. of Trace Elements & Experimental Medicine 1998; 11:119–135.

Petrus EJ et al, Randomized, Double–Masked, Placebo–Controlled Clinical Study of the Effectiveness, of Zinc Acetate–Lozenges on Common Cold Symptoms In Allergy–Tested Subjects. Current Therapeutic Research, 1998; 59(9):595–607.

* cited by examiner

*Primary Examiner*—Gary Geist

(57) ABSTRACT

This invention relates to the composition and method of treating arthritis, repairing of articular joint surfaces and the relief of symptoms associated with arthritis. The composition comprises a nitric oxide synthase inhibitor and amino sugars. The nitric oxide synthase inhibitor reduces the level of nitric oxide, the free radical believed responsible for the degradation of articular cartilage. Amino sugars are the building blocks of articular cartilage and have anti-inflammatory actions.

7 Claims, No Drawings

METHOD AND COMPOSITION FOR TREATING ARTHRITIS

This application is a continuation-in-part of Ser. No. 09/149,241 filed Sep. 9, 1998, now abandoned.

FIELD OF THE INVENTION

The present invention concerns compositions and methods of treating arthritis, repairing of articular joint surfaces and relief of symptoms associated with arthritis.

BACKGROUND OF THE INVENTION

Arthritis, a musculoskeletal disorder, is the leading cause of disability in the United States. The Centers for Disease Control and Prevention (CDC) stated that arthritis and other rheumatic conditions accounted for about 744,000 hospitalizations and 4 million days of care in 1997. Forty million Americans, representing 15% of the population, have some form of arthritis, and that figure is expected to increase to 59.4 million (18.2%) by the year 2020, an increase of 57% in the number of persons affected. Arthritis patients make more than 315 million physician visits and are hospitalized more than 8 million times a year. Arthritis costs the nation $65 billion annually in medical costs and lost productivity. Osteoarthritis (OA), or degenerative joint disease, is the most common type of arthritis, affected 20.7 million people (12.1%) of U.S. adults in 1990, now estimated at 37 million, and trailed chronic heart disease as the leading cause of Social Security payments due to long-term absence from work. Lawrence R C, et al. *Arthritis & Rheumatism* 1998;41:778–799.

Osteoarthritis usually presents as pain, which worsens with exercise or simply an X-ray that clearly shows thinning cartilage. Common joints affected are the knees, hips and spine, finger, base of thumb and base of the big toe. Osteoarthritis is characterized by degenerative changes in the articular cartilage and subsequent new bone formation at the articular margins. The primary defect in hyaline cartilage, at the articular surface of the joint, is an alteration in the ratio of total glycosaminoglycans to that of the collagen fiber content in the matrix. Yasuda K. *Hokkaido Igaku Zasshi* 1997 Jul;72(4):369–76. Paleontologists have found osteoarthritis to exist in almost every vertebrate. Joint cartilage consists of only 5 percent cells, and joint cartilage lesions do heal Tindall W N. *Business & Health Dec* 1997;47–48. Bones directly underneath the cartilage in joints is called subchondral bone. This bone nourishes the cartilage with oxygen, water, and nutrients conveyed through microscopic channels. This supply route carries "chondroprotective agents" from the bloodstream to the cartilage.

Cartilage is the supporting structure of the body, but has no blood vessels, nerves or lymphatics, and consists of thick bundles of fibrous protein (collagen) which are woven to form the articular surface. Proteoglycans fill the extracellular spaces not occupied by collagen, and are a combination of protein and sugar. Each proteoglycan subunit contains a protein core attached to hundreds of long chains of specially modified sugars called glycosaminoglycans (GAGS). Glucosamine is the single most important component and precursor for GAGs. Glucosamine is almost completely absorbed by the GI tract into the bloodstream. Cartilage rebuilding is only as good as its GAG synthesis. Chondrocytes in the cartilage obtain glucosamine from the subchondral blood vessels and manufacture N-acetylglucosamine (NAG) and glucuronic acid, which make hyaluronan, which is half glucosamine, and provides the lubricating ability of joints.

There is no definitive answer regarding the cause of osteoarthritis. A natural erosion of cartilage occurs with age, but excessive loads placed on joints, obesity, heredity, trauma, decreased circulation, poor bone alignment, and repetitive stress motion play a role. Osteoarthritis may also be the result of free radical damage, thought to be a major cause of many diseases, including the aging process, cancer, heart disease and degenerative diseases.

Free radicals affect the immune system causing rheumatoid arthritis and osteoarthritis. Free radicals are atoms or atomic groups that are byproducts of normal metabolism, tobacco smoke, pollutants, car exhaust, bacteria, radiation, and chemicals which oxidize or damage otherwise healthy cells. They damage DNA, corrode cell membranes, and may play a role in the development of cancer, heart and lung disease, cataracts, and cause or accelerate the aging process. Bucci wrote that there is conclusive evidence that free radicals do most of their damage in rheumatoid arthritis, but also to the cartilage in osteoarthritis. Bucci L. *Healing Arthritis the Natural Way Arlington*, Tex.: Summit Publishing Group, 1995, pp. 34–5. In his best seller, Theodosakis stated that "Osteoarthritis may be the result of free radical damage. And to make matters worse, joint inflammation itself may trigger an even faster rate of new free radical formation. Prevention of free radical damage is a critical feature in treating and preventing osteoarthritis." Theodosakis J, Adderly B, Fox B. *The Arthritis Cure* New York, St. Martin's Press, 1997, p 147–9. Unless the damage caused by free radical formation is addressed, any benefits obtained by using only chondroprotective agents could be nullified; similar to trying to fill a sieve with water, the relief is transient but pathology progresses.

There is no known drug that claims to reverse osteoarthritis. Most therapeutic agents are directed at reducing the inflammation and relieving pain. Non-steroidal anti-inflammatory drugs (NSAIDs) are the first line of treatment for osteoarthritis, but long-term use can lead to gastric ulcers, kidney damage, hearing loss and even inhibit cartilage formation.

SUMMARY OF THE INVENTION

This invention relates to the composition and method of treating arthritis, repairing of articular joint surfaces and the relief of symptoms associated with arthritis. The nitric oxide synthase inhibitor reduces the level of nitric oxide, the free radical responsible for the degradation of articular cartilage. Amino sugars are the building blocks of articular cartilage and have anti-inflammatory actions.

DESCRIPTION OF THE PREFERRED EMBODIMENTS

Osteoarthritis is thought to be the result of decreased production and increased degradation of the cartilaginous matrix. Loss of this protective layer leads to roughening and fissuring of the cartilage and may eventually cause erosion severe enough to expose the bone. The current goal of osteoarthritis therapy is the relief of pain. NSAID use is limited by the fact that they do not change the natural course of the disease and may accelerate joint deterioration in the long run.

Nitric Oxide Synthase Inhibitors

The maintenance of articular cartilage requires a balance between anabolic and catabolic processes. An increase in some cytokines, such as interleukin-1 (IL-1), is associated with a decrease in the synthesis and increase in the degradation of proteoglycans and collagens necessary for the structural integrity of the cartilaginous matrix. While cytokines, such as transforming growth factor β(TGF β), stimulates chondrocyte synthesis of collagens and proteoglycans, reduces the activity of IL-1-stimulated proteinases, and opposes the inhibitory and catabolic effects of IL-1.

Patients presenting with either rheumatoid arthritis (RA) or osteoarthritis (OA) have been observed to have increased levels of NO in the synovial fluid. A significant source of NO production in these patients appeared to be articular chondrocytes. Henrotin YE, et al, Nitric oxide downregulates cytokines, *J of Rheumatology* 1998;25(8):1595–1601. Nitric oxide (NO) is produced by articular chondrocytes in large amounts for extended periods of time by an inducible form of nitric oxide synthase (NOS) in response to activation by IL-1 and other agents. An increase in NO decreases the synthesis of proteoglycans and type II collagen. If NO production is blocked with the use of $N^G$-monomethyl-L-arginine (L-NMA), an inhibitor of NOS, inhibition of proteoglycan synthesis by IL-1β is blocked, and concentration of TGF β is increased. Studer R K, Georgescu H I, Miller L A, Evans C H, Inhibition of transforming growth factor β production by nitric oxide-treated chondrocytes, *Arthritis & Rheumatism* 1999;42(2):248–257.

Nitric oxide is a short lived, gaseous free radical that is synthesized from the terminal guanidino nitrogen of L-arginine in an oxidation reaction catalyzed by NOS. NOS expression is inducible by endotoxin, cytokines, growth factor and immune complexes. The overexpression of NOS in rheumatoid arthritis (RA) may result from increased levels of tumor necrosis factor-α (TNF-α), IL-1β, and other proinflammatory cytokines characteristic of this disease. Chondrocytes from patients with OA and RA spontaneously over express NOS and produce elevated levels of NO. St. Clair E W, Nitric oxide—friend or foe in arthritis? *J of Rheumatology* 1998;25(8):1451–1453.

Canadian researchers reduced the progression of experimental osteoarthritis in dogs by inhibiting inducible nitric oxide synthase (NOS). Pelletier J P, et al. *Arthritis & Rheumatism* 1998;41:1275–1286. Pelletier reported that osteoarthritis cartilage produced an increased amount of nitric oxide (NO) due to an increased level of inducible nitric oxide synthase in cartilage chondrocytes. Nitric oxide plays an important role in autoimmunity and inflammation. Normal cartilage does not produce NO or express NOS unless stimulated with cytokines. In the joint, NO, produced in response to cytokine stimulation, exerts a number of catabolic effects on chondrocyte functions which would be expected to promote the degradation of articular cartilage. These effects of NO on chondrocytes include: inhibition of collagen and proteoglycan synthesis, activation of metalloproteinases, increased susceptibility to injury by other oxidants, inhibition of actin polymerization, and apoptosis. NSAIDs, such as aspirin, and to a lesser extent, sodium salicylate, and tetracycline inhibit the expression of NOS protein. Clancy R M, Amin A R, Abramson S B. *Arthritis & Rheumatism* 1998;41:1141–1151.

Nitric oxide synthase inhibitors which may be employed include, but are not limited to: arginine-based analogues such as methylated arginines, substituted L-arginine, nitro-arginine, L-$N^G$-nitroarginine, $N^G$-mono-methyl-L-arginine (NMA), N-nitro-L-arginine methyl ester, N-amino-L-arginine, N-methyl-L-arginine, $N^G$-monomethyl-L-arginine (L-NMA), L-$N^G$-mono-methyl-arginine (L-NMMA); flavoprotein binders such as diphenylene iodonium and related iodonium derivatives, ornithine and ornithine derivatives such as N-imino-ethyl-L-ornithine; tetracycline; L-canavanine; citrulline; redox dyes such as methylene blue; calmodulin binders such as trifluoropiperazine and calcinarin; heme binders; zinc compounds; tetrahydropterin analogs such as aminoguanidine; and depleters of biopterin such as methotrexate.

The use of NOS inhibitors is well known in the art. Dawson et al, U.S. Pat. No. 5,266,594, discloses a method of preventing or treating glutamate neurotoxicity with a NOS inhibitor capable of penetrating the blood brain barrier. Ahluwalia et al, U.S. Pat. No. 5,468,476, discloses a method of reducing hair growth with a NOS inhibitor. Wahl et al, U.S. Pat. No. 5,449,688, discloses a method for treating chronic inflammatory conditions by parenterally or intravenously administering a NOS inhibitor. Stamler et al, U.S. Pat. No. 5,545,614, discloses a method for stimulating skeletal muscle contractions with a NOS inhibitor. Moncada et al, U.S. Pat. No. 5,585,402, discloses a method for inhibiting tissue damage by using a NOS inhibitor to decrease NO production in vascular endothelial cells. Dunn et al, U.S. Pat. No. 5,665,757, discloses a method for treating anxiety using a NOS inhibitor. Mjalli et al, U.S. Pat. No. 5,723,451, discloses a method for inhibiting NOS using one of eleven formulations. None of the above cited patents teach or suggest the use of the composition and method outlined in the present invention.

Amino Sugars

Agents that may repair, or at the very least, slow the degradation of articular cartilage have been described as possessing chondroprotective properties. Examples of these agents include: heparinoids (Arteparon, Rumalon), hyaluronic acid, piroxicam, tetracyclines, corticosteroids, chondroitin, and glucosamine sulfate. Da Camara C C, Dowless G V. *Annals of Pharmacotherapy* 1998;32:580–7.

Glucosamine from exogenous sources (food and supplements) may stop the progression of cartilage degradation and stimulate the production of new cartilage. Glucosamine absorbed by the gastrointestinal tract undergoes significant first-pass metabolism in the liver, with the resulting 26% bioavailibility. It is incorporated into plasma proteins as a result of hepatic metabolism, and concentrates in the articular cartilage. Clinical improvement of symptoms has been seen as early as one week after oral administration of glucosamine sulfate and has persisted for up to four weeks after discontinuation. Barclay T S, Tsourounis C, McCart G M. Glucosamine. *Annals of Pharmacotherapy* 1998;32:574–79.

Several commercial forms of glucosamine are available, including the sulfate, hydrochloride, and N-acetylglucosamine (NAG). Glucosamine hydrochloride has a higher concentration of glucosamine than the sulfate form. NAG is rapidly metabolized to make proteins and provides less glucosamine for cartilage repair. The composition of the invention could include one or a combination of the glucosamine forms. Patients have reported a more rapid response with higher dosages of glucosarine, but the therapeutic results with glucosamine alone have not been consistent. The dosage range for glucosamine can vary from 500 mg to 3000 mg a day, in divided doses, depending on body weight and severity of symptoms. One approach is to take 1,500 mg of glucosamine daily until symptoms have decreased, then reduce the dosage to 1,000 mg for two weeks and eventually stop treatment after symptoms cease or stay on a maintenance dose of 500 mg per day.

Adverse effects reported from glucosamine are gastrointestinal, such as heartburn and epigastric pain.

Because the half-life of glucosamine in the blood is relatively short, a sustained-release form of the compound could avoid the adverse effects and provide a more uniform blood level. Talent J M, Gracy R W. *Clinical Therapy* 1996; 18(6):1184–90.

The use of amino sugars is well known in the art. Jacobi, U.S. Pat. No. 3,859,436, discloses a topical composition of glucose, fructose, glucosamine and desoxyribose and ribose. Prudden, U.S. Pat. No. 4,006,224, discloses a method for treating inflammatory disorders of the gastrointestinal tract with D-glucosamine. Meisner, U.S. Pat. No. 4,590,067, discloses a composition for the prevention and treatment of periodontal disease comprising, bone meal, tyrosine, glucosamine and ascorbic acid. Speck, U.S. Pat. No. 4,870,061, discloses a method for treating degenerative joint disease by buccal administration of N-acetylglucosamine. Kludas, U.S. Pat. No. 5,036,056, discloses a method for treating damaged connective tissue with a connective tissue matrix of collagens, proteoglycans, glycosaminoglycans and glycoproteins. Henderson, U.S. Pat. Nos. 5,364,845 and 5,587,363, discloses a composition for the repair of connective tissue comprising glucosamine, chondroitin sulfate and manganese. Williams et al, U.S. Pat. No. 5,679,344, discloses a composition for articular disorders comprising glucosamine and proteases. Diaz et al, U.S. Pat. Nos. 5,795,576 and 5,891,441, discloses a composition and method for the elimination of undigested fat prior to digestion comprising, psyllium, glucosamine, glucomannan, apple pectin and stearic acid. Murad, U.S. Pat. No. 5,804,594, discloses an oral composition for improving skin conditions comprising, N-acetylglucosamine, ascorbic acid, amino acids, and a transition methal composition. Florio, U.S. Pat. No. 5,840,715, discloses a composition of nutritional supplements of gamma linolenic acid, eicosapentaenoic acid and docosahexaneoic acid, chondroitin sulfate, N-acetylglucosamine sulfate, glucosamine sulfate and manganese aspartate. Platt, U.S. Pat. No. 5,891,861, discloses a composition of oligomers of beta glucosamine to treat fungal diseases. Weisman, U.S. Pat. No. 5,888,514, discloses a composition of natural ingredients for treating bone and joint inflammation using shark cartilage, glucosamine, herbs and enzymes. None of the above cited patents teach or suggest the composition or method outlined in the present invention.

Chondroitin sulfate is the major GAG in cartilage, and has a synergistic effect with glucosamine, but poorly absorbed by oral administration. Chondroitin sulfate is half galactosamine, which is made directly from glucosamine, and has great water retaining ability. Dosage range of chondroitin sulfate is 250 mg to 1,000 mg per day in divided doses. Morrison, U.S. Pat. No 3,895,107, discloses a method of inhibiting atherosclerotic lesions by administering chondroitin sulfate. Walton et al, U.S. Pat. No. 4,489,065, discloses the binding of drugs to chondroitin for the controlled release of the drug. None of the above cited patents teach or suggest the use of the composition and method outlined in the present invention.

Zinc Compounds

Zinc plays a physiological role in the regulation of bone metabolism, by stimulating bone formation and mineralization and an inhibitory effect on bone resorption. Zinc activates aminoacyl-tRNA synthetase in osteoblastic cells, stimulates cellular protein synthesis, and inhibits osteoclast-like cell formation in marrow cells. Bone zinc content is decreased by development, with aging, skeletal unloading, and postmenopausal conditions. Zinc plays a role in the preservation of bone mass. Most zinc compounds, such as zinc sulfate, are useful for the prevention of osteoporosis, but a recent study confirmed that β-Alanyl-L-histidinato zinc (AHZ) has a potent effect on bone formation and calcification. Yamaguchi M, Role of Zinc in Bone Formation and Bone Resporption, *J. of Trace Elements and Experimental Medicine* 1998; 11:119–135.

Zinc compounds have anti-inflammatory and anti-infective properties. In a recent published article, Petrus E J et al., *Current Therapeutic Research,* 1998; 59/9: 595–607, the inventor served as chief investigator for a randomized, double-masked, placebo-controlled clinical study of the effectiveness of zinc acetate lozenges on common cold symptoms in allergy-tested subjects. Those subjects who used the zinc lozenges had both a shorter duration and severity of common cold symptoms. Those subjects who were positive for allergies, were more responsive to zinc by having a shorter duration of nasal symptoms. The study cited many references that reported the benefits and effects of zinc compounds.

Zinc is an essential mineral found in every form of life on earth. Unlike other metals, zinc is virtually nontoxic. Zinc and its compounds have long been recognized as possessing certain therapeutic functions. Zinc compounds are acknowledged as astringents and beneficial in wound healing, reducing inflammation, and has antimicrobial, antifungal and antiviral activity. Zinc is the active agent in formulations to treat diaper rash, decubitus ulcers, and abrasions. Zinc stabilizes the cell membranes and inhibits the formation of free radicals. Zinc also strengthens the integrity of blood vessel walls by reducing the membrane permeability and stopping bleeding.

Zinc has an inhibitory effect on the release of histamine from mast cells due to its stabilizing effect of the mast cell membrane. Mast cells isolated from specimens of atherosclerotic plaques contained matrix metalloproteinase type 9, one of the enzymes that can produce collagen degradation. Kovanen Pt, et al. *J. Am College of Cardiology* 1998;32:606–612. The inhibitory effect of zinc on allergy and immunology make it an excellent enhancement to glucosamine and chondroitin therapy. Zinc is also a very potent inhibitor of nitric oxide synthase (NOS). Cuajungco M P, Lees G J *Neurobiol Disease* 1997;4(3–4):137–69.

In a preferred form of the invention, the composition uses a zinc salt such as zinc acetate, with the dosage range of 30 to 60 mg per day in divided doses. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

Zinc acetate is absorbed throughout the small intestine and has an excellent safety profile. It does not adversely alter serum albumin, bilirubin, aminotransferases, hematologic variables, iron metabolism or renal function indices. Zinc acetate has been assigned to FDA pregnancy category A, indicating that the possibility of fetal abnormalities appears remote. In several trials, no toxic adverse effects have been reported in any patient. The most common adverse effect of zinc therapy is gastrointestinal irritation, which is reported to occur in approximately 10% of patients. Anderson L A, Hakojarvi A L, Boudreaux S K. *Annals of Pharmacotherapy* 1998;32:78–87. A controlled-release formulation could reduce GI irritation and enhance absorption.

Although any suitable route of administration may be employed for providing the subject with an effective dosage of the composition according to the methods of the present invention, oral administration is preferred. Suitable routes include, for example, oral, rectal, parenteral, intravenous, topical, transdermal, subcutaneous, intramuscular, and like forms of administration may be employed. Suitable dosage forms include tablets, troches, dispersions, suspensions, solutions, capsules, patches, suppositories, creams, ointments, gels, and the like, although oral dosage forms are preferred. A topical composition, with a permeation enhancing amount of at least one penetration enhancer, in an appropriate pharmaceutical carrier, could be in the form of a gel, ointment, cream, solution or other means.

Enteric Coating

The use of pharmaceutical controlled release methods to deliver the composition to the gastrointestinal tract with a desired level of nitric oxide synthase inhibitors, amino sugars and other agents without the adverse gastrointestinal effects is well known in the art.

Enteric coatings are pH sensitive polymers designed to remain intact in the acidic environment of the stomach, but to dissolve in the more alkaline environment of the intestine. Some enteric coatings use blends of cellulose acetate phthalate polymers. Wu et al, U.S. Pat. No. 5,356,634 discloses an enteric coating composition of cellulose acetate phthalate (CAP) and cellulose acetate trimellitate polymers. Crook et al, U.S. Pat. No. 5,723,151 discloses a composition of cellulose acetate phthalate polymer and organic solvent. Some enteric coatings use polyvinylpyrrolidone (PVP). Sipos, U.S. Pat. No. 4,079,125 discloses a binder and stabilizer of PVP and a coating of CAP and diethyl phthalate. Patell, U.S. Pat. No. 4,775,536 discloses the use of an enteric polymer of an acrylic resin and an undercoat and overcoat of PVP. Hodges et al, U.S. Pat No. 5,225,202 discloses an enteric coated composition of hydroxypropylmethyl cellulose phthalate, a plasticizer of triethyl citrate and talc as an anti-adherent.

Some polymers commonly used for enteric coatings are cellulose acetate phthalate (CAP), hydroxypropyl methylcellulose phthalate (HPMCP), cellulose acetate trimellitate (CAT), hydroxypropyl methylcellulose acetate succinate (HPMCAS), polyvinyl acetate phthalate (PVAP) and acrylic resins. One formulation of the present invention uses 7 mg of polyvinylpirrolidone to coat the immunostimulant composition. The composition can be in the form of a tablet, capsule, granules, or pill for oral administration. Disintegration of the PVP enteric coating occurs in approximately 40 minutes, about the time the composition is in the intestine.

In addition to nitric oxide synthase inhibitors and amino sugars, the following active agents may supplement the composition to promote the development and maintenance of cartilage, include but are not limited to: vitamins, A, B, C, E; minerals, selenium, silica, manganese, magnesium, copper and boron; glycosaminoglycans; analgesics, anti-inflammatory agents, methyl-sulfonyl-methane, Sadenosyl-methionine, alpha-lipoic acid, aloe vera extract, preservatives, antioxidants, stabilizers, surfactants, anti-infective agents, adjuvants, anthocyanidins, proanthocyanidins, and herbal derivatives.

In a further aspect of this invention, for those who have difficulty swallowing a large tablet, due to esophageal strictures or other pathology, a therapeutically effective solution can be administered by a suspension of the active agents in a pharmaceutically acceptable carrier to provide a liquid form to be swallowed or sprayed onto the oral mucosa. By a "pharmaceutically acceptable carrier" is meant a composition, solvent, dispersion medium, coating, delivery vehicle or the like, which can be employed to administer the compositions of the present invention without undue adverse physiological effects.

Although illustrative embodiments of the invention have been shown and described, a wide range of modifications, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention. The above-mentioned patents are hereby incorporated by reference.

This invention is further illustrated by the following examples which are to be regarded as illustrative only, and in no way limit the scope of the invention.

EXAMPLE 1

A 58 year old male with diagnosed osteoarthritis of both knees was started on a commercial composition of glucosamine hydrochloride 500 mg and chondroitin sulfate 400 mg taken three times a day for six months. The relief from pain and limitation of motion was inconsistent. A new composition, of the invention, comprising zinc acetate 20 mg and glucosamine sulfate 500 mg coated with polyvinylpirrolidone 7 mg taken three times a day was commenced. By the $21^{st}$ day of treatment with the new formulation, the knee pain subsided and range of motion was unrestricted. A maintenance dose of glucosamine sulfate 500 mg and zinc acetate 10 mg was then continued for six months and the pain relief and range of motion of the knees were maintained.

EXAMPLE 2

A 59 year old male with diagnosed osteoarthritis of the right foot with severe pain on running. He started on a commercial composition of a glucosamine complex (glucosamine hydrochloride, N-Acetylglucosamine and glucosamine sulfate) 500 mg and chondroitin sulfate 400 mg, taken three times a day for three months. The pain relief was inconsistent and required supplemental analgesics in order to obtain relief A new composition, of the invention, comprising zinc acetate 20 mg and glucosamine sulfate 500 mg coated with polyvinylpirrolidone 7 mg taken three times a day was commenced. By the second week of treatment with the new formulation, the foot pain subsided and he was able to run and resume his tennis playing. A maintenance dose of glucosamine sulfate 500 mg and zinc acetate 10 mg was then continued for five months and the pain relief and ability to run and play sports continued.

EXAMPLE 3

A 12 year old Weimaraner developed weakness of his hind legs which limited his ability to jump and lift his leg to urinate. He was evaluated by the College of Veterinary Medicine at Texas A&M University and started on prednisone 20 mg per day but with limited success. He was then started on the new composition, of the invention, comprising zinc acetate 20 mg and glucosamine sulfate 500 mg coated with polyvinylpirrolidone 7 mg taken twice a day. After three weeks of treatment with the new formulation, he demonstrated increased strength of his hind legs and regained his ability to lift his leg on urinating and no pain on deep palpation of the hips. He was then maintained on glucosamine sulfate 500 mg and zinc acetate 10 mg, twice a day for 11 months until his death. While on the maintenance dose he continued to demonstrate strength in his hind legs.

Although illustrative embodiments of the invention have been shown and described, a wide range of modifications, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A method for treating arthritis in mammals by administering a therapeutically effective amount of a composition comprising
    a) an inhibitor of nitric oxide synthase, and
    b) an aminosugar.
2. The method of claim 1, wherein said aminosugar in the composition is selected from the group consisting of: glucosamine, glucosamine hydrochloride, glucosamine sulfate, N-acetyl-glucosamine, and mixtures thereof.
3. The method of claim 1, wherein the composition optionally contains additional agents selected from the group consisting of glycosaminoglycans, vitamin A, vitamin B, vitamin E, selenium, silica, manganese, magnesium, copper, boron, analgesics, anti-inflammatory agents, methyl-sulfonyl-methane, S-adenosylmethionine, alpha-lipoic acid, aloe vera extract, antioxidants, anti-infective agents, adjuvants, anthocyanadins, proanthocyanadins, and herbal derivatives, and mixtures thereof.
4. The method of claim 1 wherein said composition has an enteric coating to deliver the composition orally in a controlled release into the gastrointestinal tract.
5. The method of claim 1, wherein the composition further comprises a carrier suitable for oral, rectal, parenteral, intravenous, topical, transdermal, subcutaneous, and intramuscular administration.
6. The method of claim 1, wherein said inhibitors of nitric oxide synthase include zinc compounds, arginine derivatives, flavoprotein binders, diphenylene iodonium and derivatives thereof, ornithine and derivatives thereof, N-imino-ethyl-L-ornithine, tetracycline, L-canavanine, citrulline, redox dyes, methylene blue, calmodulin binders, trifluoropiperazine, calcinarin, heme binders, tetrahydropterin derivatives, aminoguanidine, depleters of biopterin, methotrexate, non-steroidal anti-inflammatory agents, sodium salicylate, and mixtures thereof.
7. The method of claim 6, wherein said arginine derivatives include methylated arginines, substituted L-arginine, nitro-arginine, L-$N^G$-nitroarginine, $N^G$-monomethyl-L-arginine (NMA), N-nitro-L-arginine methyl ester, N-amino-L-arginine, N-methyl-L-arginine, $N^G$-monomethyl-L-arginine (L-NMA), and L-$N^G$-monomethylarginine (L-NMMA).

* * * * *